United States Patent [19]

Siegler

[11] Patent Number: 5,228,454
[45] Date of Patent: Jul. 20, 1993

[54] APPARATUS AND METHOD FOR DETERMINING LOAD-DISPLACEMENT AND FLEXIBILITY CHARACTERISTICS OF A JOINT

[75] Inventor: Sorin Siegler, Merion, Pa.

[73] Assignee: Drexel University, Philadelphia, Pa.

[21] Appl. No.: 738,972

[22] Filed: Aug. 1, 1991

[51] Int. Cl.⁵ .................................... A61B 5/103
[52] U.S. Cl. .................................... 128/782; 128/779
[58] Field of Search .................. 128/779, 782, 774; 73/862.08, 862.19, 862.23, 862.38, 862.62, 862.65, 862.68, 379

[56] References Cited

U.S. PATENT DOCUMENTS

| | | | |
|---|---|---|---|
| 4,062,355 | 12/1977 | Kaye | 128/779 |
| 4,306,571 | 12/1981 | McLeod, Jr. | 128/782 |
| 4,323,080 | 4/1982 | Melhart | 128/774 |
| 4,549,555 | 10/1985 | Fraser et al. | 128/782 |
| 4,583,554 | 4/1986 | Mittelman et al. | 128/774 |
| 4,804,000 | 2/1989 | Lamb et al. | 128/774 |
| 4,823,807 | 4/1989 | Russell et al. | 128/773 |
| 4,909,262 | 3/1990 | Halpern et al. | 128/774 |
| 5,014,719 | 5/1991 | McLeod | 128/774 |
| 5,099,859 | 3/1992 | Bell | 128/781 |

FOREIGN PATENT DOCUMENTS 8804536 6/1988 PCT Int'l Appl. .............. 128/774

OTHER PUBLICATIONS

Lowe et al, "Knee Analyser . . . Knee" Med. & Biol. Eng. & Comput. vol. 15, No. 5, pp. 548-552, Sep., 1977.

Primary Examiner—Max Hindenburg
Assistant Examiner—Guy V. Tucker
Attorney, Agent, or Firm—Panitch Schwarze Jacobs & Nadel

[57] ABSTRACT

An apparatus which determines the load-displacement and flexibility characteristics of an anatomical joint. The apparatus includes a first frame for receiving a first body portion and a second frame for receiving a second body portion which is pivotable with respect to the first body portion. A pivot assembly is interconnected between the first frame and the second frame such that the second frame is pivotable with respect to the first frame about first and second frame pivot axes. The body portions are positioned on the frames such that the first and second joint pivot axes are generally aligned with the first and second frame pivot axes, respectively. Angular potentiometers are used to determine the angular displacement of the second frame with respect to the first frame about at least one of the first and second frame pivot axes upon application of at least one force to the second body portion. Torque sensors are also provided for determining a torque about at least one of the first and second frame pivot axes upon application of the force. The determined angular displacement and torque are indicative of the load-displacement and flexibility characteristics of the joint.

6 Claims, 5 Drawing Sheets

APPARATUS AND METHOD FOR DETERMINING LOAD-DISPLACEMENT AND FLEXIBILITY CHARACTERISTICS OF A JOINT

FIELD OF THE INVENTION

The present invention relates generally to determining the load-displacement and flexibility characteristics of a joint and, more particularly, to an apparatus and method for determining load-displacement and flexibility characteristics of the joint in a clinical or experimental environment.

BACKGROUND OF THE INVENTION

To date, the clinical assessment of joint pathology, such as ligament injuries, equinus and other joint deformities, is subjective in nature. The clinician primarily relies on the manual manipulation of the joint. During clinical examination, the clinician obtains a subjective "feel" for the amount of laxity or stiffness that is present in the involved joint as compared to the clinician's previous experience regarding what the normal joint stiffness should feel like and/or as compared with the intact contralateral joint. This clinical examination is then supplemented by the patient clinical history and by radiological evaluations. Moreover, the assessment of the effectiveness of treatment, be it cast therapy, surgery, etc., is completely subjective and relies to a great extent on feedback from the patient. Consequently, there is a need for a quantitative, reliable technique to assess the flexibility of a joint for the purposes of contributing to the clinical management of joint pathologies.

Aside from the need for a more objective assessment of joint pathologies, there is also a need for providing an objective analysis in the design and evaluation of footwear. That is, there is a need to determine the level of support (three dimensional load-displacement and flexibility characteristics) provided to a joint such as the ankle joint by athletic footwear and to evaluate the quality of fit of this footwear. Currently, athletic shoes and other foot and ankle supporting devices are designed purely on an intuitive basis. There is no objective means for determining the quantitative support provided by a particular footwear design to provide the designer with sufficient feedback to rationally modify the design of the footwear for better performance.

The present invention is directed to an apparatus and method which will allow a clinician and footwear designer to determine the load-displacement and flexibility characteristics of a joint and footwear, respectively. The present invention is directed to ascertaining the angular and linear displacement of the joint about and along its pivot axes produced in response to applied torques and forces about and along the axes. Accordingly, the present invention provides an objective quantitative, reliable technique to assess the load-displacement and flexibility characteristics of anatomical joints which greatly contributes to the clinical management of joint pathologies as well as to the design of footwear.

SUMMARY OF THE INVENTION

Briefly stated, the present invention relates to an apparatus for determining load-displacement and flexibility characteristics of an anatomical joint. The joint is formed by a first body portion and a second body portion such that the second body portion is pivotable with respect to the first body portion about a first joint pivot axis and a second joint pivot axis. The apparatus comprises a first frame for receiving the first body portion. The first frame includes first securing means for securely mounting the first body portion to the first frame. A second frame receives the second body portion. The second frame includes second securing means for securely mounting the second body portion to the second frame. Pivot means are interconnected between the first frame and the second frame such that the second frame is pivotable with respect to the first frame about a first frame pivot axis and a second frame pivot axis. The first and second body portions are respectively positionable on the first and second frames such that the first and second joint pivot axes are generally aligned with the first and second frame pivot axes, respectively. Means are provided for determining an angular displacement of the second frame with respect to the first frame about at least one of the first and second frame pivot axes upon application of at least one force to one of the second frame, the second body portion and the pivot means. Means is also provided for determining a torque about at least one of the first and second frame pivot axes upon application of the force whereby the determined angular displacement and the determined torque are indicative of the load-displacement and flexibility characteristics of the joint.

BRIEF DESCRIPTION OF THE DRAWINGS

The foregoing summary, as well as the following detailed description, will be better understood when read in conjunction with the appended drawings. For the purpose of illustrating the invention, there is shown an embodiment which is presently preferred, it being understood, however, that this invention is not limited to the precise arrangements and instrumentalities shown. In the drawings.

DESCRIPTION OF THE PREFERRED EMBODIMENT

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the apparatus and designated parts thereof. The terminology includes the words above specifically mentioned, derivatives thereof and words of similar import.

Referring now to the drawings in detail, therein like numerals indicate like elements throughout, there is shown in FIGS. 1 through 4 and 6 a preferred embodiment of an apparatus 10 for determining load-displacement and flexibility characteristics of a body joint such as an ankle joint 12 (shown in phantom). It is preferred that the joint 12 be attached to a first body portion 14 and a second body portion 16 such that the second body portion 16 is pivotable with respect to the first body portion 14 about a first joint pivot axis 18, a second joint pivot axis 20 and a third joint pivot axis 22, as shown in FIGS. 5A through 5C.

Figure 5A:
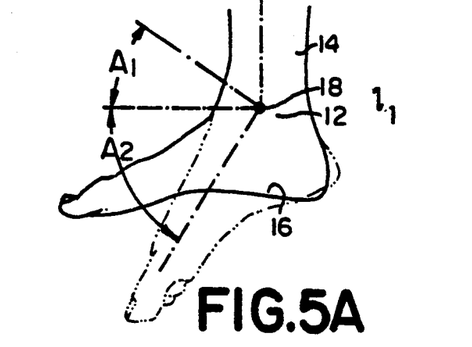
FIGS. 5A through 5F show the six degrees of freedom about which the apparatus of FIG. 1 permits the ankle joint to move.
Figure 5B:
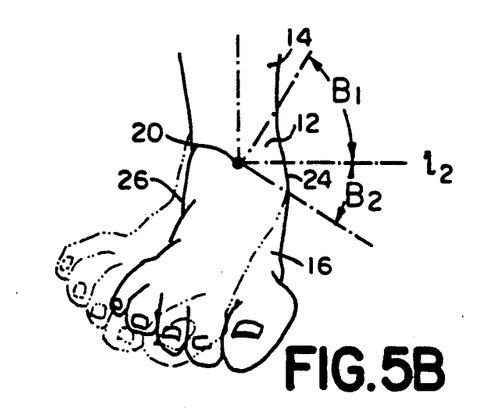
Figure 5C:
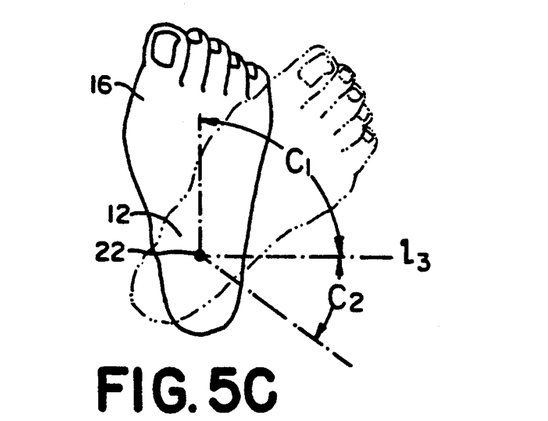

Referring now to FIGS. 5A through 5C, in the present embodiment, the anatomical joint 12 is an ankle joint. It is understood by those skilled in the art that the present invention is not limited to any particular anatomical joint. For instance, the present invention is equally applicable to the wrist, elbow, knee, shoulder and any other joint of the human body. Moreover, the present invention is not limited to body joints with any particular number of pivot axes. For example, the body joint could have one or two pivot axes without departing from the spirit and scope of the invention. Moreover, it is understood by those skilled in the art that the present invention is equally applicable to non-human body joints, such as the ankle joint of a monkey or ape.

As shown in FIGS. 5A through 5C, the first, second and third joint pivot axes 18, 20 and 22 of the joint 12 extend generally perpendicularly with respect to each other. The first joint pivot axis 18 of the joint 12 is aligned with the tip 24 of the medial malleolus and the tip 26 of the lateral malleolus (see FIGS. 5B and 5F). As shown in FIG. 5A, relative motion between the calcaneus and the tibia (not shown) about the first joint pivot axis 18 results in dorsiflexion $A_1$/plantarflexion $A_2$ of the joint 12. The second joint pivot axis 20 is generally perpendicular to the first joint pivot axis 18 and intersects the first pivot axis 18 at approximately halfway between the tip 24 of the medial malleolus and the tip 26 of the lateral malleolus. As shown in FIG. 5B, relative motion between the calcaneus and the tibia about the second joint pivot axis 20 results in inversion $B_1$/eversion $B_2$ of the joint 12. The third joint pivot axis 22 extends generally perpendicularly to the first and second joint pivot axes 18, 20 and intersects the first and second joint pivot axes 18, 20 at the same point where the first and second joint pivot axes 18, 20 intersect each other. As shown in FIG. 5C, relative motion between the calcaneus and tibia about the third joint pivot axis 22 results in internal rotation $C_1$/external rotation $C_2$ of the joint 12.

Figure 5D:
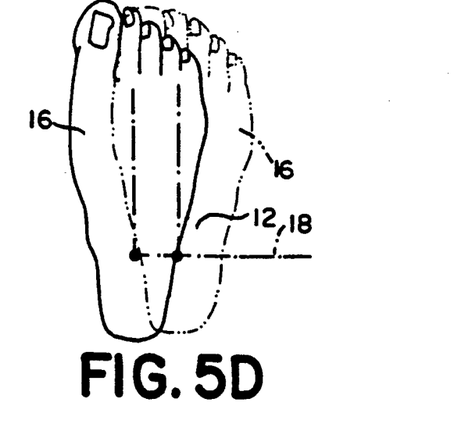
Figure 5E:
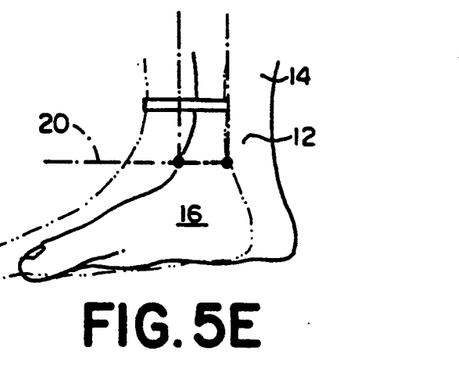
Figure 5F:
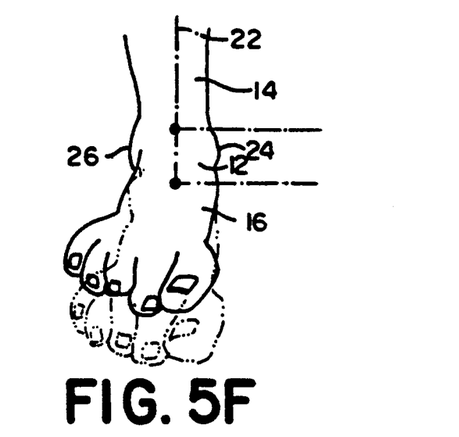

Referring now to FIGS. 5D through 5F, the first body portion 14 is linearly displaceable with respect to the second body portion 16 along the first, second and third joint pivot axes 18, 20, 22. While linear displacement between the first body portion 14 and the second body portion 16 is normally minimal when the joint 12 is in an uninjured state, if injury occurs linear displacement may increase between the first body portion 14 and the second body portion 16. Accordingly, in evaluating the extent of injury or the effectiveness of treatment, it is desirable to ascertain the linear displacement of the joint 12.

As shown in FIG. 5D, the second body portion 16 is shown in a first or normal (solid) position and a second or injured (phantom) position along the first joint pivot axis 18. In FIG. 5E, the second body portion 16 is similarly shown in two positions along the second joint pivot axis 20. In FIG. 5F, the second body portion 16 is also shown in two positions along the third joint pivot axis 22.

The above-described joint parameters are well-known to those skilled in the art, as set forth in the article "The Three-Dimensional Kinematics and Flexibility Characteristics of the Human Ankle and Subtalar Joints—Part I: Kinematics" by Siegler et al., published in the *Journal of Biomechanical Engineering*, Vol. 110, p. 364–374, November 1988, which is hereby incorporated by reference.

Unless otherwise indicated herein, it is understood that all of the elements of the apparatus 10 are preferably constructed of a high-strength, lightweight metallic material, such as aluminum. However, it is understood by those skilled in the art that the present invention is not limited to constructing the apparatus 10 of any particular material and that the apparatus 10 could be constructed of other high-strength, lightweight materials, such as a composite fibrous and resin material or any suitable polymeric material.

Figure 1:
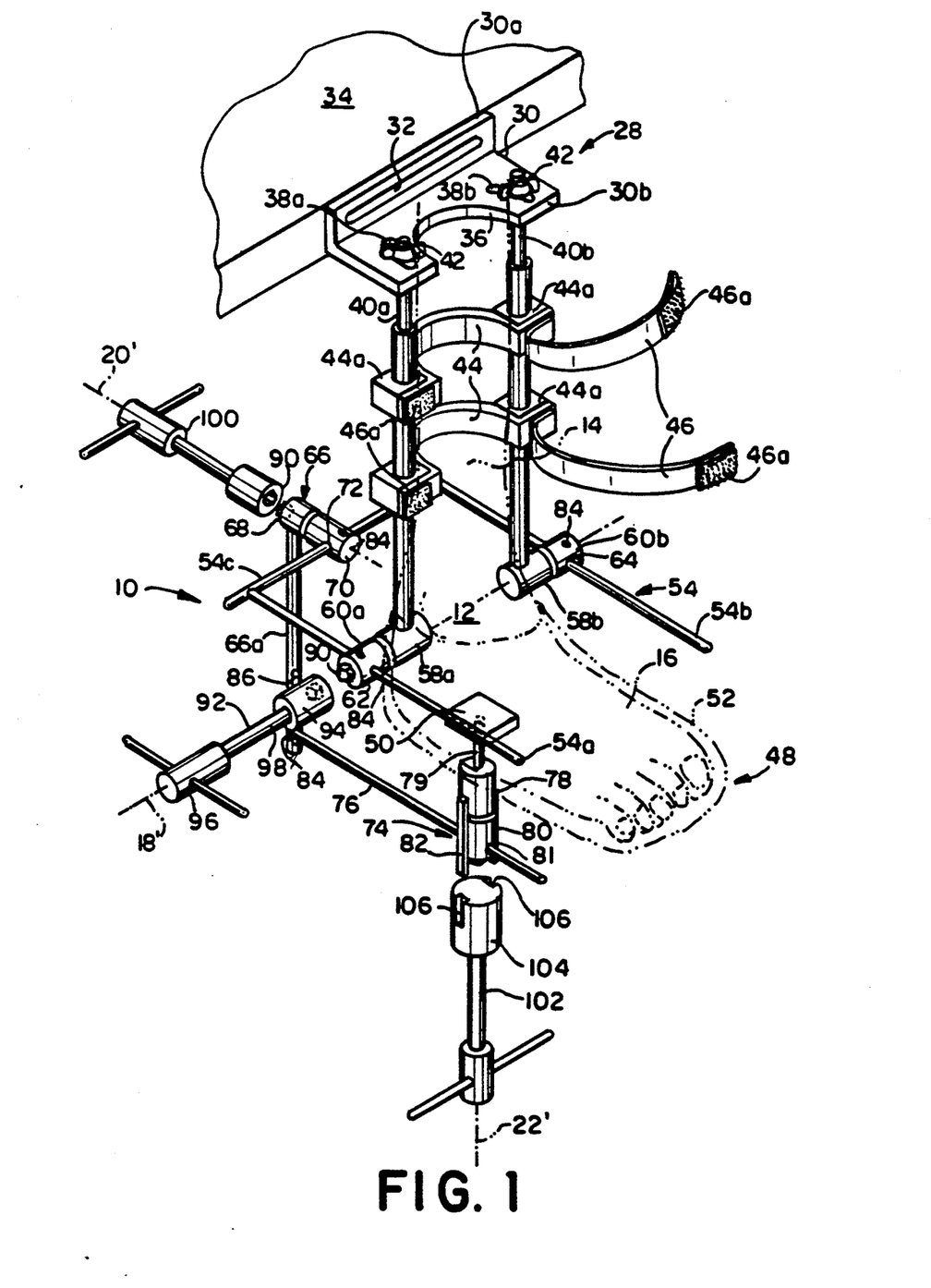
FIG. 1 is a perspective view of an apparatus in accordance with the present invention.
Figure 2:
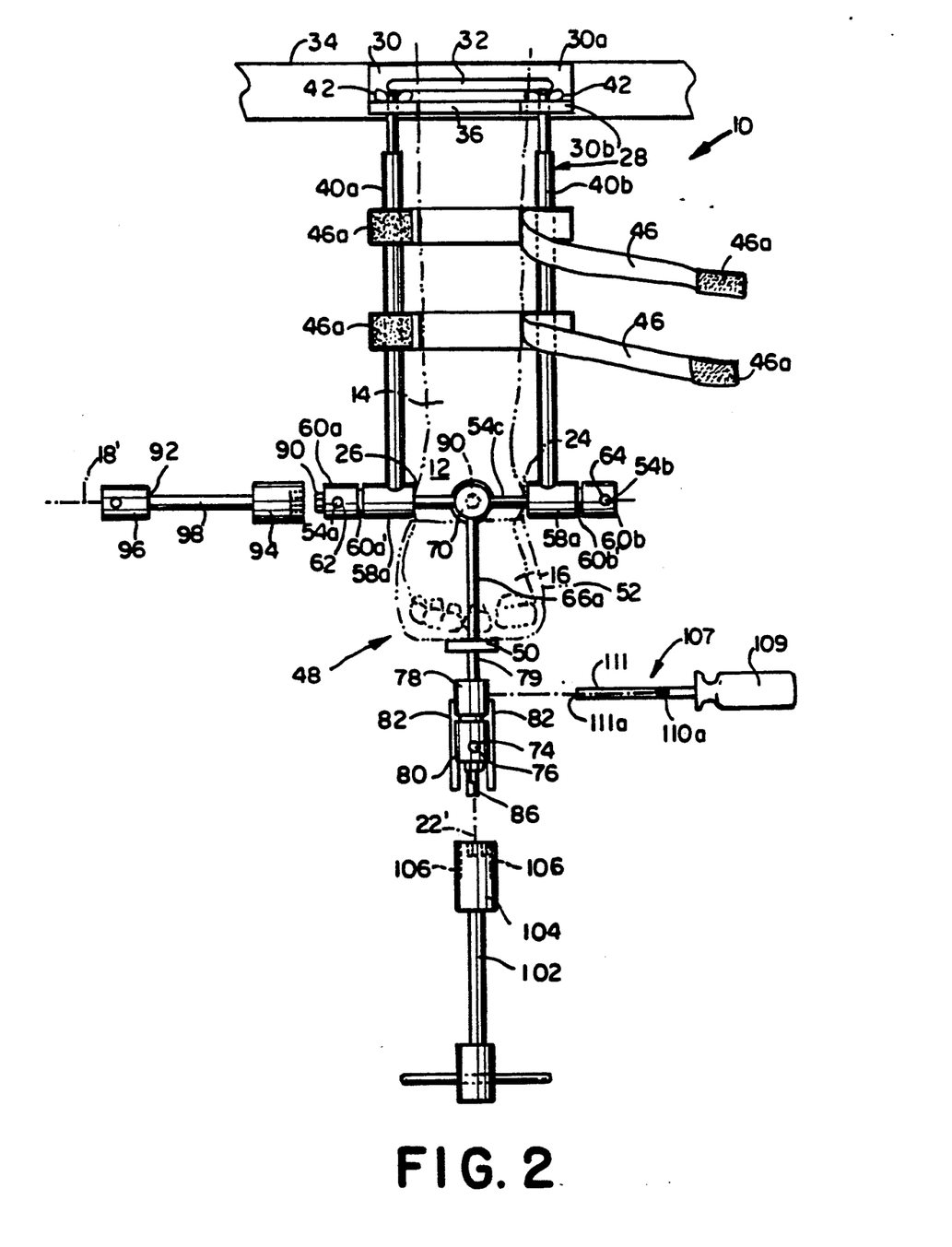
FIG. 2 is a front elevational view of the apparatus shown in FIG. 1.
Figure 3:
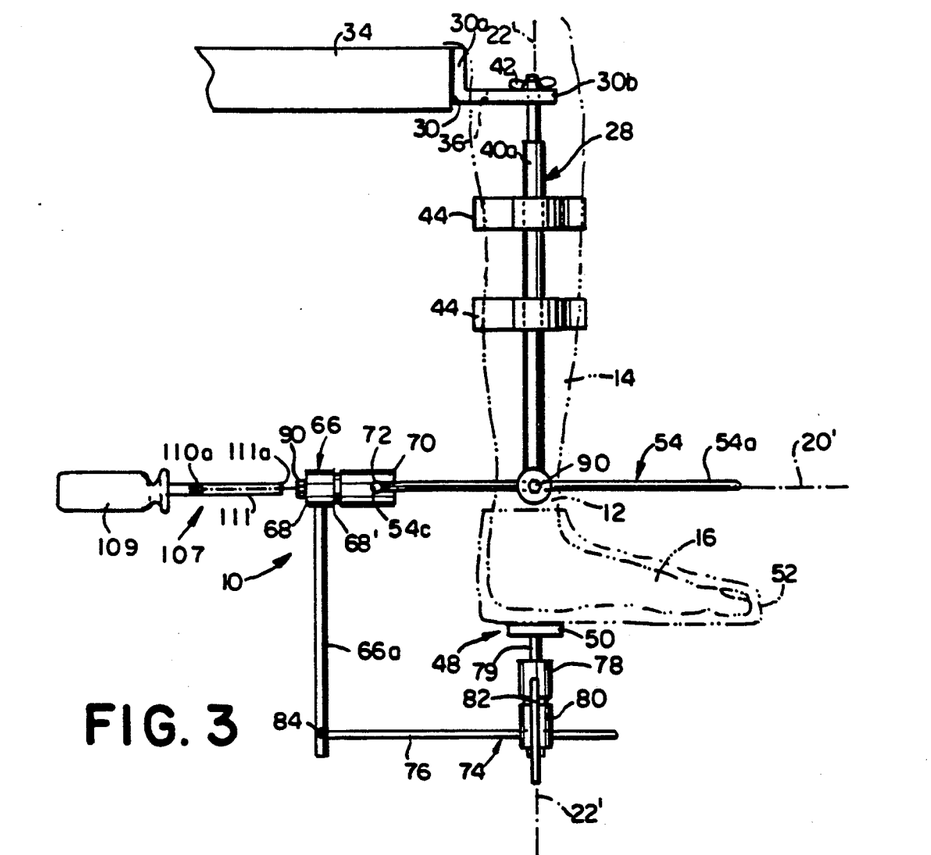
FIG. 3 is a left side elevational view of the apparatus shown in FIG. 1.

Referring now to FIGS. 1 through 3, the apparatus 10 includes a first frame 28 for receiving the first body portion 14. The first frame 28 includes a generally L-shaped mounting bracket 30 having a first leg 30a and a second leg 30b which extend generally perpendicularly with respect to each other. The first leg 30a is preferably secured to the edge of a table or other support structure 34 for receiving the remaining body of the patient to be tested (not shown). The first leg 30a includes a generally longitudinal slot 32 for receiving a fastener (not shown), such as a screw, therethrough for securing the mounting bracket 30 to the edge of the table 34.

Figure 4:
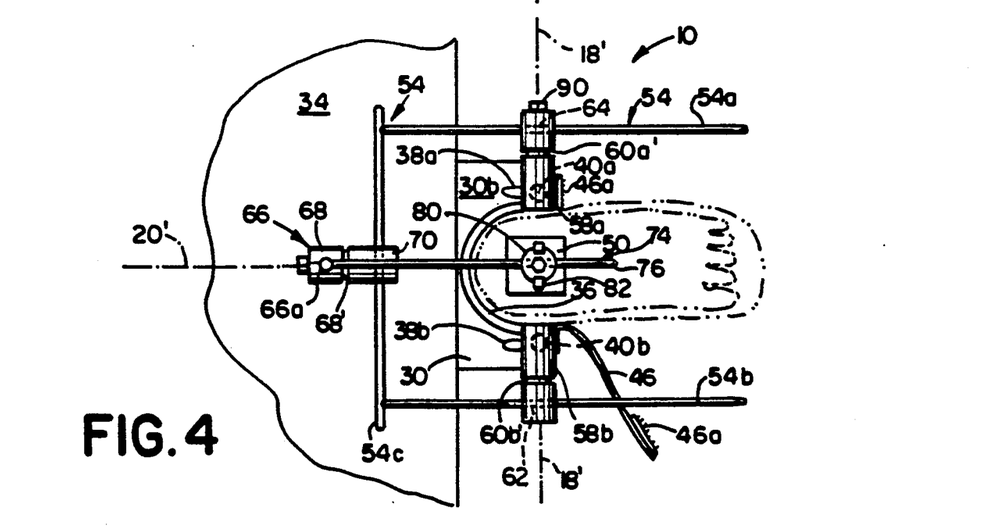
FIG. 4 is a bottom plan view of the apparatus shown in FIG. 1.

As best shown in FIGS. 1 and 4, the second leg 30b includes a generally semicircular cutout 36 for receiving the first body portion 14 or, in the present embodiment, a leg of the patient whose joint is to be tested. The second leg 30b further includes a first generally arcuate slot 38a and a second generally arcuate slot 38b extending therethrough and complementarily positioned for slideably receiving a first generally elongate bar 40a and a second generally elongate bar 40b, respectively. The first and second slots 38a, 38b permit the first and second bars 40a, 40b to move with respect to the second leg 30b of the mounting bracket 30 for allowing the first body portion 14 to be appropriately positioned on the first frame 28, as described in more detail hereinafter. The upper ends of the first and second bars 40a, 40b are threaded for securably and threadably receiving a nut, such as a wing nut 42, on each side of the second leg 30b to assist in firmly securing the first and second bars 40a, 40b to the second leg 30b of the mounting bracket 30.

The first and second bars 40a, 40b preferably extend generally parallel with respect to each other and are spaced a sufficient distance to complementarily receive the first body portion 14 therebetween. Further, the first and second bars 40a, 40b are preferably generally linear and have a generally circular cross section. However, it is understood by those skilled in the art that the first and second bars 40a, 40b could be non-linear to conform to the shape of the first body portion 14 and could be of other cross-sectional configurations, such as square, rectangular or elliptical. Moreover, while it is preferred that the first and second bars 40a, 40b be adjustably mounted on the second leg 30b of the mounting bracket 30, it is understood by those skilled in the art that other means could be provided for adjusting the relative position of the first and second bars 40a, 40b with respect to the mounting bracket 30. For instance, a ratchet mechanism (not shown) which would permit quick adjustment of the first and second bars 40a, 40b with respect to the mounting bracket 30 could also be utilized.

While it is preferred that the first and second bars 40a, 40b be secured to a table 34 through the mounting bracket 30, it is understood by those skilled in the art that the first and second bars 40a, 40b can be secured to other devices with or without the use of a mounting bracket 30. For instance, the first and second bars 40a, 40b could be secured to a chair (not shown) in a similar manner. Thus, the present invention is not limited to mounting the apparatus 10 on any particular device so long as the apparatus 10 is generally stable.

As shown in FIGS. 1 and 4, the first frame 28 includes first securing means for securely mounting the first body portion 14 to the first frame 28. In the present embodiment, it is preferred that the first securing means be comprised of a pair of generally U-shaped members 44 spaced apart vertically and extending between the first and second bars 40a, 40b for receiving the first body portion 14. The U-shaped members 44 preferably include suitably sized apertures 44a extending through the ends thereof for slideably receiving the first and second bars 40a, 40b, as shown in FIG. 1. Set screws (not shown) are used to firmly secure the U-shaped members 44 in a desired position along the first and second bars 40a, 40b. The first securing means further preferably comprises a woven strap 46 associated with each U-shaped member 44. Hook and loop material 46a is provided on one end of each woven strap 46 and on one end of each of the U-shaped members 44.

To secure the first body portion 14 to the frame 28, the first body portion 14 is positioned between the first and second bars 40a, 40b in engagement with the U-shaped members 44. The straps 46 are then wrapped around the first body portion 14 to engage the hook and loop material 46a to thereby securely retain the first body portion 14 on the first frame 28.

While it is preferred that the first securing means be comprised of the two U-shaped members 44 and two straps 46, it is understood by those skilled in the art that other means can be utilized for securing the first body portion 14 to the first frame 28. For instance, the straps 46 could be replaced with generally U-shaped members (not shown) which are pivotally mounted to one end of the U-shaped members 44 and include some type of fastener for securing the U-shaped members together when the first body portion 14 is positioned therebetween. Furthermore, other means could be utilized to secure the straps 46 to the U-shaped members 44. For example, a clamp or buckling arrangement (not shown) could be utilized.

Referring now to FIGS. 1 and 3, the apparatus 10 includes a second frame 48 for receiving the second body portion 16. The second frame 48 in the present embodiment is comprised of a generally rectangular plate 50 positioned beneath the second body portion 16. The second frame 48 includes second securing means for securely mounting the second body portion 16 to the second frame 48 or plate 50. In the present embodiment, the second securing means is preferably comprised of a shoe 52, such as a sneaker (not shown), for securely receiving the second body portion 16 or foot of the person to be analyzed. The plate 50 is securely mounted to the bottom of the shoe 52 by a suitable fastener, such as an adhesive or by standard hardware.

While it is preferred that the second securing means be comprised of a shoe connected to the plate 50, it is understood by those skilled in the art that other means can be utilized to secure the second body portion 16 to the second frame 48. For instance, the plate 50 could be sized to correspond to the width of the second body portion 16 and include side walls extending upwardly therefrom for receiving the second body portion 16 therebetween. Moreover, where the apparatus 10 is utilized in conjunction with a body joint other than the ankle joint, it is clear that other means would be required to secure the second body portion 16 to the second frame 48. For instance, use of the apparatus 10 in connection with the elbow joint, would require that the second securing means be comprised of a sleeve or the like (not shown) for receiving the forearm of the patient.

Referring now to FIGS. 1 through 4, a pivot means is interconnected between the first frame 28 and the second frame 48 such that the second frame 48 is pivotable with respect to the first frame 28 about a first frame pivot axis 18', a second frame pivot axis 20', and a third frame pivot axis 22'. It is preferred that the first, second and third frame pivot axes 18', 20', 22' extend generally perpendicular with respect to each other and have a common point of intersection regardless of the position of the pivot means. The first and second body portions 14, 16 are preferably respectively positionable on the first and second frames 28, 48 such that the first, second and third joint pivot axes 18, 20, 22 are generally aligned with the first, second and third frame pivot axes 18', 20' and 22', respectively.

As best shown in FIGS. 1, 3 and 4, the pivot means preferably comprises a first assembly 54 secured to the first frame 28. The first assembly 54 preferably includes first hinge means interconnected between the first assembly 54 and the first frame 28 for allowing the first assembly 54 to pivot with respect to the first frame 28 to define the first frame pivot axis 18'.

As shown in FIGS. 1 and 4, the first assembly 54 includes a first elongated member 54a and a second elongated member 54b extending generally parallel with respect to each other and respectively positioned proximate the distal ends of the first and second bars 40a, 40b. A third elongated member 54c is secured between the first and second elongated members 54a, 54b and extends generally perpendicular with respect to the first and second elongated members 54a, 54b. It is preferred that the third elongated member 54c be secured to the ends of the first and second elongated members 54a, 54b positioned rearwardly of the joint 12 such that the first, second and third elongated members 54a, 54b, 54c form a structure which is generally U-shaped in plan view (FIG. 4). It is understood by those skilled in the art that the third elongated member 54c could be secured to the ends of the first and second elongated members 54a, 54b positioned forwardly of the joint 12, without departing from the spirit and scope of the invention.

In the present embodiment, it is preferred that the first hinge means of the first assembly 54 be comprised of a first barrel 58a and a second barrel 58b secured to the distal ends of the first and second bars 40a, 40b, respectively. Further, a first cylinder 60a, having a suitably sized aperture 62 extending therethrough for slideably and complementarily receiving the first elongated member 54a, is pivotally mounted to the first barrel 58a. Similarly, a second cylinder 60b, having a suitably sized aperture 64 extending therethrough for complementarily and slideably receiving the second elongated member 54b therethrough, is pivotally mounted to the second barrel 58b.

As best shown in FIGS. 2 and 4, the first and second cylinders 60a, 60b are pivotable with respect to the first and second barrels 58a, 58b, respectively because each cylinder 60a, 60b includes a rod 60a', 60b' which extends towards the joint 12 into a correspondingly sized aperture (not shown) in the first and second barrels 58a, 58b, respectively. The rods 60a' and 60b' are preferably sized and positioned to permit the cylinders 60a, 60b to rotate with respect to the first and second barrels 58a, 58b about the first frame pivot axis 18' and thereby allow the entire first assembly 54 to rotate with respect to the first frame 28 about the first frame pivot axis 18'.

Referring now to FIGS. 1 and 3, the pivot means further comprises a second assembly 66 secured to the first assembly 54. The second assembly 66 includes a second hinge means interconnected between the first assembly 54 and the second assembly 66 for allowing the second assembly 66 to pivot with respect to the first assembly 54 to define the second frame pivot axis 20'. The second assembly 66 is preferably comprised of an elongated member 66a having at one end thereof a cylinder 68. The cylinder 68 is preferably rotatably secured to a barrel 70 which includes a suitably sized aperture 72 extending therethrough for complementarily and slideably receiving. The third elongated member 54c of the first assembly 54.

The barrel 70 is preferably positioned on the third elongate member 54c such that the longitudinal axes thereof is positioned generally equidistantly between the first and second elongated members 54a, 54b to thereby form the second frame pivot axes 20' (FIG. 3). A rod 68' extends from the cylinder 68 into a suitably sized aperture (not shown) in the barrel 70 for permitting the cylinder 68 to rotate with respect to the barrel 70. The cylinder 66, rod 68' and barrel 70 interact to form the second hinge means which permits the second assembly 66 to pivot with respect to the first assembly 54 to define the second frame pivot axis 20'.

As best shown in FIGS. 1 through 3, the pivot means further includes a third assembly 74 interconnected between the second assembly 66 and the second frame 48. The third assembly 74 includes third hinge means interconnected between the third assembly 74 and the second frame 48 for allowing the third assembly 74 to pivot with respect to the second frame 48 to define the third frame pivot axis 22'. The third assembly 74 is comprised of an elongated member 76 secured to the elongated member 66a of the second assembly 66 at the end thereof opposite from the cylinder 68. The elongated member 76 of the third assembly 74 preferably extends from the elongated member 66a of the second assembly 66 a distance sufficient to be positioned beneath the second frame 48.

In the present embodiment, it is preferred that the third hinge means be comprised of a cylinder 78 fixably secured to the plate 50 and rotatably secured to a barrel 80 which is affixed to the elongated member 76 of the third assembly 74. The cylinder 78 is secured to the plate 50 by a threaded rod 79 which permits the distance between the plate 50 and cylinder 78 to be adjusted for assisting in properly aligning the joint 12 on the apparatus 10. It is preferred that the barrel 80 include an aperture 81 extending therethrough for slideably receiving the elongated member 76 of the third assembly 74. A set screw (not shown) is provided in the barrel 80 for locking the elongated member 76 of the third assembly 74 thereto.

The barrel 80 is rotatably with respect to the cylinder 78 in a manner generally identical to that described above in connection with the first and second assemblies 54 and 66, except that a pair of bars 82 are fixably secured to the periphery of the cylinder 78 and extend downwardly around and beyond the barrel 80 for receiving a torque applicator, described in more detail hereinafter. That is, rotation of the bars 82 causes the cylinder 78 and plate 50 to rotate with respect to the barrel 80.

The pivot means further includes linear displacement means for allowing the second frame 48 to be linearly displaced with respect to the first frame 28 along at least one of the first, second and third frame pivot axes 18', 20', 22'. As used herein, the term "along" is broadly construed to mean parallel and/or aligned. To allow the first frame 28 to be linearly displaced with respect to the second frame 48 along the first frame pivot axis 18', the third elongated member 54c of the first assembly 54 is slideably mounted in the aperture 72 of the second assembly barrel 70. As such, the second assembly 66, the third assembly 74 and the second frame 48 can be moved along the third elongated member 54c. To prevent the second assembly 66 from moving with respect to the third elongated member 54c, a set screw 84 is provided in the barrel 70, as is understood by those skilled in the art.

To allow the second frame 48 be linearly displaced with respect to the first frame 28 along the second frame pivot axis 20', the first and second elongated members 54a, 54b of the first assembly 54 are slideably disposed in the apertures 62, 64 of the first and second cylinders 60a, 60b, respectively. The first and second elongated members 54a, 54b can be fixably secured to the first and second cylinders 60a, 60b by a set screw 84 provided in the first and second cylinders 60a, 60b.

To allow the second frame 48 to be linearly displaced with respect to the first frame 28 along the second frame pivot axis 20', the first and second elongated members 54a, 54b of the first assembly 54 are slideably disposed in the apertures 62, 64 of the first and second cylinders 60a, 60b, respectively. The first and second elongated members 54a, 54b can be fixably secured to the first and second cylinders 60a, 60b by a set screw 84 provided in the first and second cylinders 60a, 60b.

To allow the second frame 48 to be linearly displaced with respect to the first frame 28 along the third frame pivot axis 22', the elongated member 76 of the third assembly 74 is slideably disposed in a slot 86 in the elongated member 66a of the second assembly 66. The elongated member 76 of the third assembly 74 can be fixed to the elongated member 66a of the second assembly 66 by a set screw 84 located in the elongated member 66a of the second assembly 66.

While in the present embodiment, it is preferred that the pivot means be comprised of a first assembly 54, a second assembly 66, and a third assembly 74 as described above, it is understood by those skilled in the art that other means can be provided for allowing the second frame 48 to be pivotable with respect to the first frame 28 about the first, second and third frame pivot axes 18', 20', 22' without departing from the spirit and scope of the invention.

Figure 6:
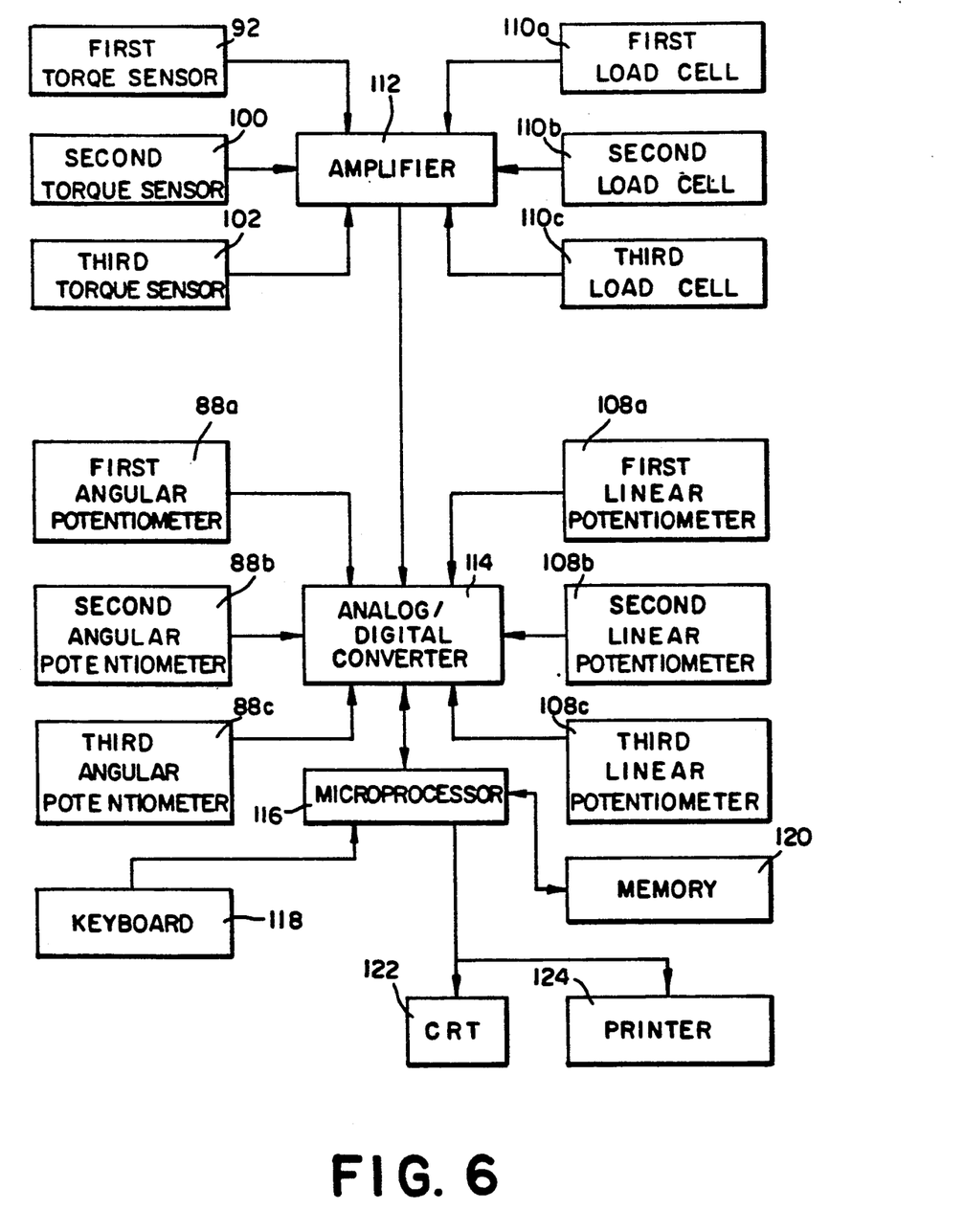
FIG. 6 is a schematic block diagram of a monitoring system for the apparatus shown in FIG. 1 in accordance with the present invention.

Referring now to FIGS. 1 and 6, the apparatus 10 further includes means for determining an angular displacement of the second frame 48 with respect to the first frame 28 about at least one of the first, second and third frame pivot axes 18', 20', 22' upon application of at least one force to one of the second frame 48, the second body portion 16 and the pivot means. In the present embodiment, it is preferred that the angular displacement determining means be comprised of first, second and third angular potentiometers 88a, 88b, 88c each being located on one of the first, second and third frame pivot axes 18', 20', 22', respectively. In the present embodiment, the first angular potentiometer 88a is formed as part of the first barrel 58a on the first assembly 54; the second angular potentiometer 88b is formed as part of the barrel 70 on the second assembly 66; and the third angular potentiometer 88c is formed as part of the barrel 78 on the third assembly 74. Angular potentiometers are well known to those skilled in the art. Accordingly, further description thereof is omitted for purposes of convenience only and is not limiting.

While force may be applied to one of the second frame 48, the second body portion 16 and the pivot means, it is preferred that a force be applied to one of the first, second or third assemblies 54, 66, 74 directly about one or more of the first, second and third frame pivot axes 18', 20', 22'. In the present embodiment, it is preferred that the cylinder 60a of the first assembly 54 and the cylinder 68 of the second assembly 66 include a bolt head 90 on the exposed end thereof for receiving a socket or the like to rotate the respective cylinder, as described in more detail hereinafter.

The apparatus 10 further includes means for determining a torque about at least one of the first, second and third frame pivot axes 18', 20', 22' upon application of the above-mentioned force. In the present embodiment, the torque determining means is comprised of a T-shaped torque sensor 92. The torque sensor 92 includes at one end thereof a socket 94 which complements the bolt head 90 on the cylinder 60a of the first assembly 54. At the other end of the torque sensor 92, a T-shaped handle is provided for allowing the clinician to grasp the torque sensor 92 to apply a torque about the first frame pivot axis 18' as well as the first joint pivot axis 18. Interconnected between the T-shaped handle 96 and the socket 94 is a torque sensing area 98 which senses the torque applied between the T-shaped handle 96 and the socket 94. The torque applied between the T-shaped handle 96 and the socket 94 corresponds to the torque applied about the first joint and frame pivot axes 18, 18'.

As shown in FIGS. 1 and 3, the torque determining means further includes a second torque sensor 100 which is generally identical to the first torque sensor except that it is arranged to apply torque to the bolt head 90 on the cylinder 68 of the second assembly 66. Torque applied through the second torque sensor 100 is applied about the second frame pivot axis 20' and the second joint pivot axis 20.

As shown in FIGS. 1 and 2, the torque determining means further includes a third torque sensor 102 for determining a torque applied about the third frame pivot axis 22'. The third torque sensor 102 is generally identical to the first and second torque sensors 92, 100 except that instead of a socket on one end of the third torque sensor 102, a coupling member 104 having a pair of corresponding grooves 106 for engagement with the bars 82 on the cylinder 78 is provided. That is, when the coupling member 104 is positioned proximate the barrel 80 with the bars 82 extending into the grooves 106, rotation of the third torque sensor 102 causes the cylinder 78 to rotate with respect to the barrel 80 and thereby causes the plate 50 and second frame 48 to rotate about the third frame pivot axis 22'.

The apparatus 10 further includes means for determining a linear displacement of the second frame 48 with respect to the first frame 28 along at least one of the first, second and third frame pivot axes 18', 20', 22' upon application of force to one of the second frame 48, the second body portion 16 and the pivot means. In the present embodiment, it is preferred that the means for determining a linear displacement of the second frame 48 with respect to the first frame 28 be comprised of first, second and third linear potentiometers 108a, 108b, 108c each being respectively positioned within the first cylinder 60a of the first assembly 54, the barrel 72 of the second assembly 66, and the slot 86 in the elongated member 66a of the second assembly 66. More particularly, the first linear potentiometer 108a measures the relative displacement of the first elongated member 54a of the first assembly 54 with respect to the first cylinder 60a as the first elongated member 54a moves within the aperture 62 of the first cylinder 60a. This relative displacement corresponds to a linear displacement of the second frame 48 with respect to the first frame 28 along the second frame pivot axis 20'.

Similarly, the second linear potentiometer 108b measures the relative displacement of the third elongated member 54c of the first assembly 54 with respect to the barrel 70 of the second assembly 66 as the third elongated member 54c moves within the aperture 72 of the barrel 70. Movement of the barrel 70 along the third elongated member 54c corresponds to linear displacement of the second frame 48 with respect to the first frame 28 along the first frame pivot axis 18'.

The third linear potentiometer 108c measures the relative displacement of the elongated member 76 of the third assembly 74 with respect to the elongated member 66a of the second assembly 66 as the elongated member 74 of the third assembly moves within the slot 86 of the elongated member 66a of the second assembly 66. The linear displacement of the elongated member 76 of the third assembly 74 with respect to the elongated member 66a of the second assembly 66 corresponds to the linear displacement of the second frame 48 with respect to the first frame 28 along the third frame pivot axis 22'.

The apparatus 10 further includes means for determining an axial force applied about the first frame pivot axis 18' and along at least one of the second and third frame pivot axes 20', 22' upon application of the force to one of the second frame 48, second body portion 16 and pivot means. In the present embodiment, it is preferred that the means for determining the axial force about or along the first, second and third frame pivot axes 18', 20', 22' be comprised of first, second and third load determining tools 107 (only one shown). Each load determining tool 107 is generally in the form of a screwdriver having a handle 109 for being grasped by the clinician and a longitudinal member 111 extending therefrom and having a blunt end 111a. The first, second and third load determining tools 107 include a first, second and third load cell 110a, 110b, 110c on the longitudinal member 111, respectively.

Referring now to FIG. 6, the first, second and third torque sensors 92, 100, 102; first, second and third load cells 110a, 110b, 110c; first, second and third angular potentiometers 88a, 88b, 88c; and first, second and third linear potentiometers 108a, 108b, 108c are each in electrical communication, through wires or the like, with a monitoring system (generally designated 115) which provides the clinician with objective data concerning the clinical assessment of the joint 12. More particularly, the monitoring system 115 includes a strain gauge conditioning amplifier unit 112 which is in electrical communication with the first, second and third torque sensors 92, 100, 102 and first, second and third load cells 110a, 110b, 110c. Thus, if the first torque sensor 92 is used to apply a torque about the first frame pivot axis 18', a signal corresponding to the applied torque is sent to the amplifier 112. The signal is amplified and forwarded to an analog to digital converter 114. The second and third torque sensors 100, 102 operate in a similar manner and may be used simultaneously with the first torque sensor 92. In addition, the first, second and third load cells 110a, 110b, 110c also forward a signal to the amplifier 112 which corresponds to an applied axial force upon sensing the same. This signal is also amplified and forwarded to the analog to digital converter 114.

In addition to receiving signals from the amplifier 112, the analog to digital converter 114 receives signals from the first, second and third angular potentiometers 88a, 88b, 88c and the first, second and third linear potentiometers 108a, 108b, 108c upon sensing the appropriate parameter in response to a force supplied to the second body portion 16, second frame 48 or pivot means. The analog to digital converter 114 then converts the signals from the various sensors to digital signals and forwards the digital signals to a microprocessor 116 which correlates the information in accordance with suitable programming. For instance, the microprocessor 116 includes an input device for inputting information into the microprocessor 116 which corresponds to the desired data to be outputted regarding the condition of the joint 12. In the present embodiment, it is preferred that the input device be a keyboard 118, as is understood by those skilled in the art. However, it is also understood by those skilled in the art that other input devices can be used, such as a floppy disk.

As shown in FIG. 6, the microprocessor 116 is in communication with a memory device 120 which receives and stores data from the various sensors which corresponds to the actual parameters sensed. That is, the various signals from the sensors are coded in some manner such that each signal can be separately identified by the microprocessor 116 and stored in identifiable locations within the memory 120. The microprocessor 116 also functions to retrieve the various sensor data from the memory 120 and converts the data into a component form for providing an output to the technician. In the present embodiment, the output is provided on a cathode ray tube (CRT) device 122 or a printer 124, as desired by the clinician through the keyboard 118. Other output devices may alternatively be used.

The memory 120 is employed to store data with respect to one or more joints of a particular patient as a result of one or more measurements which may be made at spaced time intervals. In addition, the memory 120 may store statistical data relating to one or more of a plurality of patients in order to establish a statistical data base to provide the clinician with expected normal or average data for a particular joint to provide a basis for comparison with the data obtained for a joint of a particular patient. Statistical data and/or normal or average data may also be set forth on printed charts (not shown). The processor may also provide an automatic comparison of the data with normal or average data to calculate joint flexibility as a percentage of the normal or average.

The method of determining load-displacement and flexibility characteristics of the joint 12 is comprised of positioning the apparatus 10 on the body joint 12 such that the first, second and third frame pivot axes 18', 20', 22' are generally aligned with the first, second and third joint pivot axes 18, 20, 22. To align the joint 12 on the apparatus 10, the first body portion 16 is securely positioned within the shoe 52. The first and second bars 40a, 40b and the plate 50 are then adjusted through the use of the nuts 42 and the threaded rod 79 until the tip 24 of the medial malleolus and the tip 26 of the lateral malleolus are aligned with the first frame pivot axis 18'. When the joint 12 is aligned with the first frame pivot axis 18', the second and third frame pivot axes 20' and 22' are then also aligned with the second and third joint pivot axes 20, 22.

A force is then applied to the second body portion 16 to cause the second body portion 16 to move with respect to the first body portion 14. In the present embodiment, it is preferred that the force be applied to the second body portion 16 through the use of the first, second and third torque sensors 92, 100, 102 either simultaneously or separately. That is, the first torque sensor 92 can apply a torque about the first frame pivot axis 18' by engaging the socket 94 with the bolt head 90 and applying a torque to the T-shaped handle 96 such that the first assembly 54 rotates about the first frame pivot axis 18'. Similarly, torques can be applied about the second and third frame pivot axes 20' and 22' through the use of the second and third torque sensors 100 and 102. In addition, if the clinician is only interested in measuring angular displacement of the joint 12 about the first, second and third frame pivot axes 18', 20', 22', the joint 12 can be hand manipulated without the use of the torque sensors 92, 100, 102.

A linear force can also be applied about or along one of the first, second and third frame pivot axes 18', 20', 22' through the use of the first, second and third load determining tools 107, either simultaneously or separately. For instance, the first load determining tool 107 can apply a torque about the frame pivot axis 18' by engaging the blunt end 111a of the elongated member 111 with the cylinder 78 generally parallel to the first frame pivot axis 18' and applying a force to the handle 109 of the first load determining tool 107 such that the second frame 48 moves with respect to the first frame 28 along the first frame pivot axis 18'. Similarly, forces can be applied along the second and third frame pivot axis 20', 22' by engaging a load determining tool 107 with the cylinder 68 of the second assembly 66 and the barrel 80 of the third assembly 74, respectively. The first, second and third load cells 110a, 110b, 110c sense the applied force. The sensed applied force is then transmitted to a monitoring system, described below.

As mentioned previously, a monitoring system 115 is in constant communication with the first, second and third angular potentiometers 88a, 88b, 88c, torque sensors 92, 100, 102, linear potentiometers 108a, 108b, 108c and load cells 110a, 110b, 110c upon application of force to one of the second body portion 16, second frame 48 and pivot means. The monitoring system 115 provides the clinician with data regarding the four parameters tested about all three axes regardless of where the force is applied. That is, torque applied about the first frame pivot axis 18' may be indirectly sensed by sensors which correspond to the other frame pivot axes 20', 22'.

Consequently, through the use of the monitoring system 115 and sensors, the clinician objectively measures the angular displacement of the second body portion 16 with respect to the first body portion 14 about the first, second and third joint pivot axes 18, 20, 22 in response to the application of the force. The clinician also objectively measures a torque about the first, second and third joint pivot axes 18, 20, 22 in response to the application of the force. Similarly, the clinician also determines the linear displacement of the second body portion with respect to the first body portion 14 along the first, second and third joint pivot axes 18, 20, 22 and determines an axial force applied about or along the first, second and third joint pivot axes 18, 20, 22 upon application of force to the second body portion 16.

The clinician can then correlate the determined angular displacement, torque, linear displacement and axial forces to ascertain the flexibility and broad-displacement characteristics of the joint 12. For instance, the determined angular displacement and torque corresponds to a flexibility characteristic of the joint. That is, if a relatively small amount of torque produces a relatively large amount of angular displacement, the joint would be more flexible than if a relatively larger amount of torque produced a lesser amount of angular displacement.

A clinician can use the present invention to determine the progress of treatment by periodically testing the joint during the healing process and comparing the objective results. Similarly, the apparatus 10 can be used to determine the extent of injury to the joint 12 in several different manners. For instance, the clinician can compare the objective results of the injured joint to the load-displacement and flexibility characteristics of the contralateral joint, to earlier data based on testing performed on the joint before injury, or to statistical norms. In addition, the apparatus can be used to determine the load-displacement and flexibility characteristics of a joint to determine the fitness of a joint compared to statistical norms prior to injury. This use, for example, would enable a clinician to check the load-displacement and flexibility characteristics of a professional athlete's joints prior to signing the athlete to a contract.

In addition, the apparatus 10 can be used to assess the performance of footwear and medical devices (i.e., braces). For instance, with respect to footwear, the joint could be first analyzed without any supporting footwear to determine the normal load-displacement and flexibility characteristics of the joint. The joint could then be fitted with the footwear to be tested and then have the same testing routine performed. By comparing the results of the two tests, the clinician will be able to determine the level of support provided to the joint as well as assisting in evaluating the quality of fit of the footwear.

From the foregoing description, it can be seen that the present invention comprises an apparatus for determining load-displacement and flexibility characteristics of a body joint. It will be appreciated by those skilled in the art, that changes could be made to the embodiment described in the foregoing description without departing from the broad inventive concept thereof. It is understood, therefore, that this invention is not limited to the particular embodiment disclosed, but is intended to cover all modifications which are within the spirit and scope of the invention as defined by the appended claims.

I claim:

1. An apparatus for determining load-displacement and flexibility characteristics of an anatomical joint, said joint being formed by a first body portion and a second body portion such that said second body portion is pivotable with respect to said first body portion about a first joint axis, a second joint axis, and a third joint axis, said apparatus comprising:
    a first frame for receiving said first body portion, said first frame including first securing means for securely mounting said first body portion to said first frame;
    a second frame for receiving said second body portion, said second frame including second securing means for securely mounting said second body portion to said second frame;
    pivoting means interconnected between said first frame and said second frame such that said second frame is pivotable with respect to said first frame about a first pivot axis, a second pivot axis, and a third pivot axis, said first and second body portions being respectively positionable on said first and second frames such that said first, second, and third joint axes are generally aligned with said first, second, and third pivot axes, respectively, said first and second joint axes remaining generally aligned with said first and second pivot axes as said first frame moves with respect to said second frame, wherein said pivoting means comprises:
    a first assembly secured to said first frame, said first assembly including first hinge means, interconnected between said first assembly and said first frame for allowing said first assembly to pivot with respect to said first frame to define said first pivot axis;
    a second assembly secured to said first assembly, said second assembly including second hinge means interconnected between said first assembly and said second assembly for allowing said second assembly to pivot with respect to the first assembly to define said second pivot axis; and
    a third assembly interconnected between said second assembly and said second frame, said third assembly including third hinge means interconnected between said third assembly and said second frame for allowing said third assembly to pivot with respect to said second frame to define said third pivot axis;
    means for applying an external torque to said joint about any and at least one of said first, said second, and said third pivot axes to cause said second body portion to move with respect to said first body portion;
    means for determining an angular displacement of said second frame with respect to said first frame about said one of said first, said second, and said third pivot axes upon application of said torque; and
    means for measuring said torque applied about said one of said first, said second, and said third pivot axes upon application of said torque whereby said determined angular displacement and said measured torque are indicative of the load-displacement and flexibility characteristics of said joint.

2. The apparatus as recited in claim 1 wherein said first and second pivot axes extend generally perpendicular with respect to each other.

3. The apparatus as recited in claim 1 wherein said pivoting means further includes means for allowing said second frame to be linearly displaced with respect to said first frame along at least one of said first and second pivot axes upon application of said torque.

4. The apparatus as recited in claim 3 further including means for determining a linear displacement of said second frame with respect to said first frame along at least one of said first and second pivot axes upon application of said torque.

5. The apparatus as recited in claim 4 further including means for applying and determining an axial force applied along at least one of said first and second pivot axes upon application of said axial force to one of said second frame and pivot means.

6. An apparatus for determining load-displacement and flexibility characteristics of an anatomical joint, said joint being formed by a first body portion and a second body portion such that said second body portion is pivotable with respect to said first body portion about a first joint axis, a second joint axis, and a third joint axis, said apparatus comprising:

- a first frame for receiving said first body portion, said first frame including first securing means for securely mounting said first body portion to said first frame;
- a second frame for receiving said second body portion, said second frame including second securing means for securely mounting said second body portion to said second frame;
- pivoting means interconnected between said first frame and said second frame such that said second frame is pivotable with respect to said first frame about a first pivot axis, a second pivot axis, and a third pivot axis, said first, second, and third pivot axes extending generally perpendicular with respect to each other, said first and second body portions being respectively positionable on said first and second frames such that said first, second, and third joint axes are generally aligned with said first, second, and third pivot axes, respectively, said first and second joint axes remaining generally aligned with said first and second pivot axes as said first frame moves with respect to said second frame and wherein said pivot axes remain perpendicular during said movement;
- means for applying an external torque to said joint about any and at least one of said first, said second, and said third pivot axes to cause said second body portion to move with respect to said first body portion;
- means for determining an angular displacement of said second frame with respect to said first frame about said one of said first, said second, and said third pivot axes upon application of said torque; and
- means for measuring said torque applied about said one of said first, said second, and said third pivot axes upon application of said torque whereby said determined angular displacement and said measured torque are indicative of the load-displacement and flexibility characteristics of said joint.

* * * * *